United States Patent [19]

Baker et al.

[11] 4,063,824
[45] Dec. 20, 1977

[54] CHEMICAL DOSIMETER HAVING A CONSTANT FLOW AIR SAMPLING PUMP

[75] Inventors: W. Barry Baker, Newark; Donald G. Clark, Wilmington, both of Del.

[73] Assignee: E. I. Du Pont de Nemours and Company, Wilmington, Del.

[21] Appl. No.: 602,093

[22] Filed: Aug. 5, 1975

[51] Int. Cl.$^2$ ............................................. F04B 49/00
[52] U.S. Cl. ........................................ 417/43; 417/63; 417/312; 417/411
[58] Field of Search ........................... 417/42–44, 417/63, 45, 413; 73/421.5, 211, 28, 30, 421.5 R

[56] References Cited

U.S. PATENT DOCUMENTS

| 1,910,202 | 5/1933 | Crago | 417/45 X |
|---|---|---|---|
| 2,889,780 | 6/1959 | Binford | 417/43 |
| 3,129,587 | 4/1964 | Hallanger | 73/211 |
| 3,198,121 | 8/1965 | Schaub | 417/43 X |
| 3,269,320 | 8/1966 | Tilley et al. | 417/12 |
| 3,410,059 | 11/1968 | Garnier | 417/413 X |
| 3,411,704 | 11/1968 | Hilgert et al. | 417/326 |
| 3,424,370 | 1/1969 | Law | 415/1 |
| 3,501,899 | 3/1970 | Allen | 417/43 X |
| 3,701,280 | 10/1972 | Stroman | 73/30 X |
| 3,814,544 | 6/1974 | Roberts et al. | 417/40 |
| 3,865,512 | 2/1975 | Deters | 417/44 X |
| 3,882,861 | 5/1975 | Kettering et al. | 417/44 X |
| 3,949,734 | 4/1976 | Edwards et al. | 417/43 X |
| 3,953,152 | 4/1976 | Sipin | 417/45 |

Primary Examiner—William L. Freeh
Assistant Examiner—Edward Look

[57] ABSTRACT

An improved chemical dosimeter for individual use which collects on a filter particles or vapors present in an air stream which is being pumped through the dosimeter at a constant rate, the improvement is the use of
a variable drive pump that is connected to the filter and that is driven by an electric motor and is controlled by a feed back circuit of an integrator and an amplifier and maintains a constant flow of air through the dosimeter;
the integrator receives a signal from a pressure switch that detects changes in the flow of the air stream through the dosimeter by a change in a pressure drop of the air which is being pumped through an orifice;
the dosimeter is worn by an individual and at the termination of a period of time, such as a work day, the filter is removed and the collected contents are analyzed by conventional techniques such as gas chromatography to determine a level of exposure of the individual using the dosimeter.

10 Claims, 3 Drawing Figures

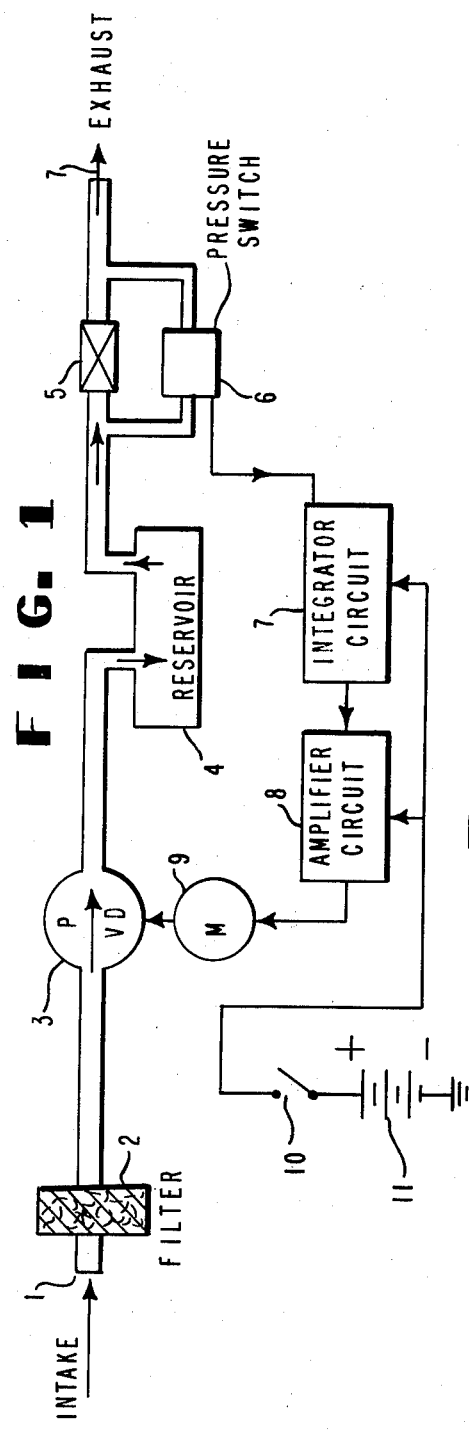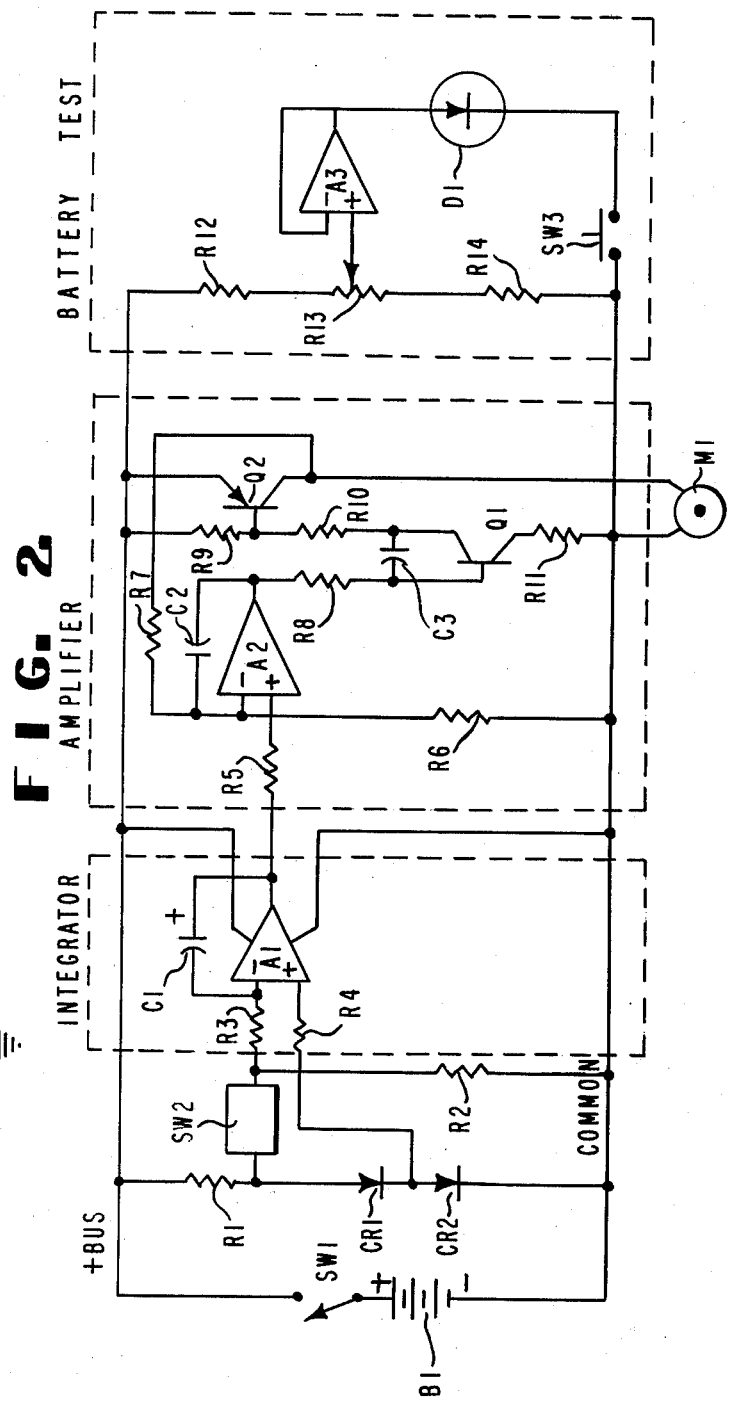

CHEMICAL DOSIMETER HAVING A CONSTANT FLOW AIR SAMPLING PUMP

BACKGROUND OF THE INVENTION

This invention relates to a dosimeter and in particular to a chemical dosimeter designed for individual use that has a constant air stream flowing through the dosimeter.

Chemical dosimeters are known and have been used by individuals in an effort to determine the level of exposure of an individual to foreign substances in air, for example, to chemical vapors or fumes, dust particles and the like. The dosimeter is worn by the individual and air is pumped through a filter which traps foreign substances in the air. At the end of an individual's exposure period, the filter is removed and analyzed for any foreign substances. The problem has been with these chemical dosimeters that the air flow rate through the dosimeter has not been accurately controlled. For example, if the filter was partially blocked so that intake of air was momentarily stopped or reduced for a period of time, it was not possible to adjust and increase the flow rate of air to compensate for the stoppage or reduction of air passing through the filter of the dosimeter. Any reduction in the air flow rate reduces the amount of foreign substances collected by the filter thereby giving an inaccurate level of exposure of the individual.

SUMMARY OF THE INVENTION

An improved chemical dosimeter for individual use that collects on a filter means particles or vapors present in an air stream which is pumped through the dosimeter at a constant flow rate; the improvement that is used therewith comprises a variable drive pump tubularly connected to the filter means and coupled to an electric motor draws the air stream through the filter means and pumps the air stream into an air reservoir;

the air reservoir connected to the pump retains excess air supplied by the pump to maintain a constant flow rate of the air stream through an orifice that is connected to the air reservoir;

the orifice is positioned in a tube attached to the reservoir and to an exhaust port, the air stream is pumped through the orifice and thereby creates an air pressure drop;

a differential pressure switch positioned in a tube connected to the exhaust port and in parallel with the orifice is activated by a change in the air pressure drop of the air stream and creates a low voltage electrical input signal that is fed to an integrator circuit;

the integrator circuit electrically connected to a power source and to the pressure switch uses the low voltage input signal generated by the pressure switch and integrates this signal into a signal that is fed into an amplifier circuit;

the amplifier circuit electrically connected to a power source and connected in series to the integrator circuit and to the electric motor amplifies the signal generated by the integrator circuit and feeds an amplified signal to the electric motor and thereby changes the speed of the motor driving the pump to maintain the air stream at a constant flow rate.

BRIEF DESCRIPTION OF THE DRAWINGS

FIG. 1 is a block diagram of the chemical dosimeter.

FIG. 2 is a schematic circuit diagram for one embodiment of the dosimeter.

DETAILED DESCRIPTION OF THE INVENTION

Figure 3:
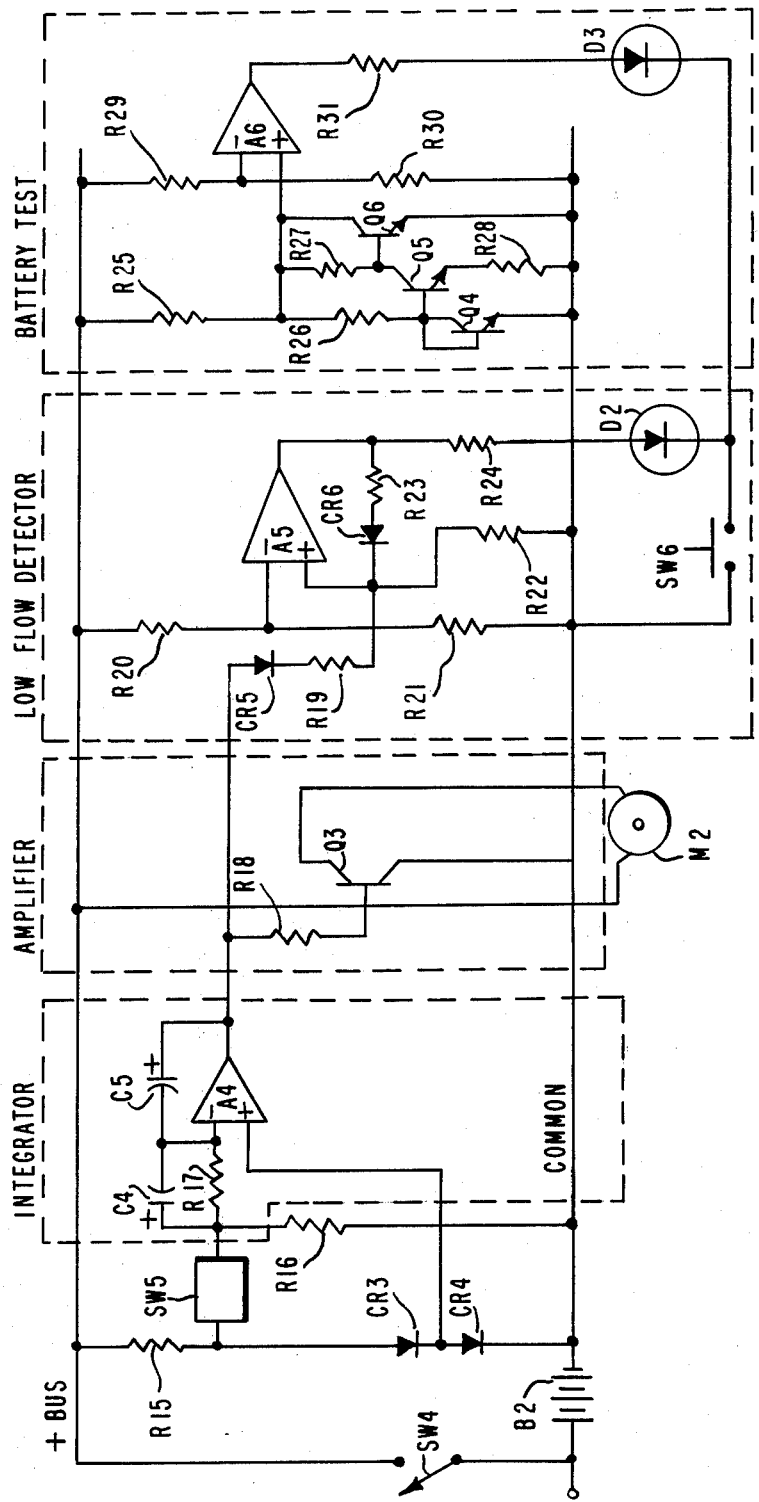
FIg. 3 is a schematic circuit diagram for one preferred embodiment of the dosimeter which contains a low air flow detector circuit and a battery test circuit.

The chemical dosimeter is designed for individual use and is compact in size and is about 1½ inches × 2 11/16 inches × 5 3/16 inches and is light in weight about 14 ounces. The dosimeter can be carried comfortably by a worker, for example, in a pocket, or a belt, in a neck band and the like, without inconvenience or hindrance to work activities. The dosimeter is of reasonable cost and is rugged in design and is well suited for service in industrial environments.

The chemical dosimeter with its constant flow feature improves the accuracy with which a wide variety of environmental hazards to individuals can be monitored. Monitoring for vinyl chloride vapors in industrial work areas and monitoring for toxic radon gas and toxic related products of radon gas in mines are typical of important applications of the dosimeter.

Referring to the block diagram of FIG. 1, a basic arrangement of the chemical dosimeter is shown. Air is pumped in at the intake 1 at a constant flow rate and passed through a filter 2. The air intake and filter are connected by a tube to a variable drive air pump 3 driven by an electric D.C. motor 9. The air is pumped to the reservoir 4 which moderates the flow level of the air and eliminates surges of air created by strokes of the pump. An orifice 5 such as an adjustable needle valve is positioned in tube leading to the exhaust port and causes an air pressure drop. A pressure switch 6 is positioned in parallel to the orifice and is activated by any change in the air pressure drop. The pressure switch 6 is electrically connected to the integrator circuit 7, which utilizes the input from the pressure switch and generates an electrical signal. The signal generated by the integrator 7 is fed to the amplifier circuit 8 which amplifies the signal and the signal controls the speed of the electric motor 9 driving the air pump 3 to provide a constant flow rate of air through the dosimeter. The integrator and the amplifier are electrically connected to a D.C. power source 11 which usually is a battery. An on-off switch 10 is positioned between the power source 11 and the amplifier and integrator circuits.

Configurations other than the above for the dosimeter can be used. For example, the orifice can be tubarly connected in series to the filter and the pump. The pump draws an air stream through the orifice and through the filter. As above, a pressure switch is in parallel relationship to the orifice and measures any change in an air pressure drop. In another example, a filter, orifice and reservoir are tubulary connected in series to a pump and the pump draws the air through the filter, orifice and reservoir. A pressure switch is positioned in parallel to the orifice to measure any change in an air pressure drop.

The filter 2 of the dosimeter can be adapted to entrap almost any type of substance such as gases, liquids of solids. If mechanical filtration is only required, for example, to collect dust particles to which a worker is exposed, a filter is provided which will entrap particles of 0.01 microns or larger. If the filter is to entrap a gas such as sulfur dioxide, a chemical filter is used which will entrap this gas. If vapors are to be entrapped, then a filter such as a charcoal filter, is used which entraps vapors. At the end of the period which an individual is wearing the dosimeter, such as an 8 hour work day, the filter is removed and examined for the substance or substances to which the individual was exposed. A simple count of particles under a microscope may be used or the filter can be analyzed, for example, with a gas chromatograph.

A variable drive air pump is used in the dosimeter. Generally, a diaphragm type pump is used that pumps from about 10 to 3000 cubic centimeters per minute. Other pumps such as piston pumps, rotary pumps and centrifugal pumps can also be used.

The pump is electrically connected to a conventional D.C. motor of about 0.0001-0.02 horsepower. The motor is a variable speed motor and operates from about 1,000 to 20,000 revolutions per minute. Under some circumstances, a reducing gear can be used between the motor and the pump.

The reservoir is usually an integral part of any framework on which the various components used in the dosimeter are mounted and is milled or cut into the framework with appropriate openings. Part of the reservoir may be enclosed with a thin sheet of an elastomer so that any pulsations of the air stream created by the pump can be readily dampened by the elastomer absorbing the pulsation.

The purpose of the reservoir is to smooth any pulsations of the air stream created by the strokes of the pump at least to some degree before the air stream passes through the orifice. Without the reservoir, a uniform flow rate of the air stream cannot be provided. The volume of the reservoir is as small as possible but of sufficient volume to reduce the pulsations of the air stream.

A typical reservoir used with a pump that pumps air at about 25 to 200 cubic centimeters per minute is about ⅛ inch by 1½ inches × ¾ inch and is covered with an elastomer about ¾ inch × 1½ inches.

An orifice such as an adjustable needle valve is positioned in a tube connecting the reservoir to the exhaust port. An orifice is used that creats a pressure drop of about 0.4-4.0 inches of water. Usually a pressure drop of 2.5-3.5 inches of water is used.

A differential pressure switch of a relatively high level of sensitivity is used and is sensitive to a pressure drop change in the air stream of about 0.1-0.5 inches of water.

The integrator circuit takes the on-off signal generated by the pressure switch and formulates a slowly changing continuous signal therefrom which is fed into the amplifier circuit. The integrator circuit is biased at about +0.6 volts and the signal from the switch increases to about 1.2 volts when the pressure switch is activated and decreases to about +0.0 volts when the switch is deactivated. The integrator circuit produces a gradually decreasing output voltage which feeds into the amplifier when the pressure switch is closed and a gradually increasing voltage when the pressure switch is open. The circuit is constructed of conventional transistors, capacitors and resistors. Examples of the circuit will be described hereinafter.

The amplifier circuit receives the signal generated by the integrator circuit and amplifies the signal so that the electric D.C. motor can be controlled at various speeds to insure a constant flow rate of the air stream through the dosimeter. The amplifier circuit amplifies the signal from the integrator to a maximum of about 96% of the total voltage of the power source. For example, for a 5 volt power source, the signal will be amplified to 4.8 volts. Generally, the amplifier has an impedance of greated than 10 ohms and up to 1 megohm. However, an amplifier with an impedance of less than 10 ohms can be used, e.g., 0.01-10 ohms impedance. The amplifier is constructed by conventional transistors, capacitors and resistors.

The power source usually is a battery of about 5-6 volts. Generally, a nickel cadmium battery of 4 cells is used. A direct current power source of rectified A.C. current can also be used.

One optional circuit that can be used in the dosimeter is a battery test circuit. The circuit uses a precision voltage detector which can be adjusted to the voltage of each cell and is set to be activated at the full charge voltage of the battery. A light emitting diode which is activated by a switch is usually used to indicate a full charge of the battery.

Another optional circuit that can be used in the dosimeter is a low air flow detector circuit which is connected to the integrator circuit and is activated when the voltage output of the integrator circuit is at higher than normal operational levels caused by an interruption of the air stream being pumped through the dosimeter. The low flow detector circuit comprises a bistable multivibrator circuit electrically connected to an indicator light such as a light emitting diode.

Referring to the circuit diagram of FIG. 2, battery B 1 which supplies power to the circuit has its negative (−) terminal connected to COMMON and its positive (+) terminal connected to power switch SW 1. The other side of SW 1 is connected to the positive (+) BUS.

Amplifier A 1 (which may be operational amplifier such as one of the four amplifiers in a type LM 324 Quad Operational Amplifier) is connected in an integrating configuration with a feedback capacitor C 1 (typically 10 microfarads). C 1 is connected from the output to the inverting (−) input of the amplifier A 1. The input resistor R 3 (typically 1 megohm) is connected to the inverting input of A 1. The values of R 3 and C 1 determine the integration rate and affect the response of the control circuit. The values are selected to give the best control with a particular pump and accumulator.

Resistor R 1 (typically 10 K ohms) is connected from the + BUS to one anode of diode, CR 1 (typically type 1N4148) and the cathode of CR 1 is connected to the anode of diode CR 2 (typically type 1N4148) which has the cathode connected to COMMON. This provides bias voltages of approximately 0.6 volt at the CR 2 anode and 1.2 volts at the CR 1 anode due to the forward voltage drops of the two diodes. The 0.6 volt point is connected to the non-inverting input (+) of the amplifier, A 1, to bias the + input at 0.6 volts above COMMON, through a resistor R 4 (typically 1 megohm) which minimizes amplifier offset voltage effects. A resistor R 2 (typically 10 K ohm) is connected from the input resistor R 3 to COMMON or ground. This provides 0.0 volts to the input resistor when pressure switch SW 2 is open. SW 2 typically is a pressure switch that operates at 3.0 inches of water pressure. The integrator produces a gradually decreasing voltage at the amplifier output when SW 2 is closed and a gradually increasing voltage when SW 2 is open. The voltage at the amplifier A 1 output is a motor speed signal which when amplified by an amplifier (described hereinafter) determines the pump motor speed. Connection from the + BUS and COMMON are made to A 1 to provide power. These connections provide power for A 2 and A 3.

The motor speed signal is applied to amplifier A 2 (typically ¼ of a type LM 324) through resistor R 5, (typically 2.2 K ohm) to the non-inverting (+) input of A 2. The amplified signal from the output of A 2 is applied to the base of transistor Q 1 (typically an NPN type 2N2926) through resistor R 8 (typically 10 K ohm). The signal from the collector of Q 1 is applied to the base of transistor Q 2 (typically a PNP Type 2N5226) through resistor R 10 (typically 1 K ohm). The output signal from the collector of Q 2 is connected to the pump motor M 1, a variable speed, direct current motor. The other side of M 1 is connected to COMMON.

The emitter of Q 1 is connected to COMMON through resistor R 11 (typically 220 ohm). Capacitor C 3, (typically 0.01 microfarad) is connected from base to collector Q 1 to reduce noise in the circuit. The emitter of Q 2 is connected to the + BUS and the base is connected to the + BUS through resistor R 9 (typically a 1 K ohm). A feedback resistor R 7 (typically 47 K ohm) is connected from the collector of Q 2 to the inverting (−) input of A 2 to provide negative feedback. The inverting input of A 2 is connected to COMMON through resistor R 6 (typically 2.2 K ohm).

Resistors R 6 and R 7 determine the overall voltage gain of the circuit from the output of A 1 to the voltage connected to the pump motor. R 7 may be adjusted to provide the optimum balance between fast control response and stable operation in pumps of various characteristics. Capacitor C 2 (typically 0.01 microfarad) is connected from the output of A 2 to the inverting input of A 2 to reduce circuit noise. This connection of A 2, Q 1, Q 2 and their associated resistor and capacitors is one of many amplifier circuits suitable for amplifying the motor speed signal from A 1 but this circuit provides a wide voltage range to the motor, typically 0 to 4.8 volts for a power supply of 5.0 volts, and provides a constant voltage output preferred in some pump configurations such as where very low motor speed for low flow is required.

A battery check circuit is built based on a special light emitting diode, D 1, (typically type HP 5082–4732 manufactured by the Hewlett-Packard Corporation) which lights at a specific level of applied voltage (typically 2.4 volts). Amplifier A 3 (typically ¼ of a type LM 324) has its inverting input (−) connected to the output providing a 1 X gain for signals applied to non-inverting input (+). The output of A 3 is connected to the anode (or + input) of D 1 and the cathode of D 1 is connected to one side of switch SW 3. The other side of SW 3 is connected to COMMON. D 1 will light if SW 3 is closed and the output of A 3 is greater than a trigger voltage (typically 2.4 volts). Resistor R 12 (typically 100 K ohm) is connected from the + BUS to one side of variable resistor, R 13 (typically a 50 K ohm potentiometer). Resistor R 14 (typically 100 K ohm) is connected from the other side of R 13 to COMMON. The wiper of R 13 is adjustable to present 2.4 volts to the noninverting input of A 3 at the desired battery voltage check level, typically 5.15 volts for a battery constructed by connecting four nickel-cadmium rechargeable cells in series.

FIG. 3 is another version of the previous circuit in which A 4 is like A 1, R 15 is like R 1, R 16 is like R 2, R 17 is like R 3, CR 3 is like CR 1, CR 4 is like CR 2, SW 4 is like SW 1, SW 5 is like SW 2, B 2 is like B 1 and C 5 is like C 1. A 4 is connected as A 1 of the previous circuit, except that the resistor in the non-inverting input is eliminated since it is not required when the amplifier offset voltage is low enough to have no effect on the integrator and except that capacitor C 4 (typically 0.5 microfarad) has been added across or in parallel with R 17 to provide faster response and more stable operation with certain pumps.

The output of A 4 is amplified by the transistor, Q 3, (typically a type 2N3053) whose base is connected to the output of A 4 via resistor R 18 (typically 2.2 K ohms), whose emitter is connected to COMMON and whose collector is connected to the pump motor, M 2. The positive (+) lead of M 2 is connected to the + BUS. This power amplifier is a less complex circuit than in FIG. 2 but provides the same 0–4.8 voltage range for the motor. The output signal of this circuit has a constant current characteristic which provides good operation with most pump configurations.

The output signal from A 4 varies from about 0 to 0.75 volts during normal control but can increase gradually on up to a saturation level of approximately 3 volts (for a power supply voltage of 4.0 volts) when the pump cannot maintain the airflow such as when the inlet tube is kinked and the airflow is blocked. To detect when the output of A 4 exceeds 2.5 volts, a low flow detector is provided. Thus, amplifier A 5 (typically ¼ of a LM 324) is connected at its inverting input to a trip voltage level. If a voltage of a greater magnitude than the trip voltage level is applied to the noninverting (+) input of A 5, the output of A 5 will change from the normal level of zero to a high level of approximately 4 volts (with a 5 volt power supply).

Resistor R 20 (typically 47 K ohm) is connected from the + BUS to resistor R 21 (typically 22 K ohm). The other side of R 21 is connected to COMMON. The junction between R 20 and R 21 is connected to the inverting (−) input of A 5.

Resistor R 23 (typically 10 K ohm) and diode CR 6 (typically a type IN 4148 are connected in series and feed the voltage from the A 5 output to the noninverting input to keep the A 5 output high even if the original voltage signal is removed. Resistor R 24 (typically 270 ohm); light emitting diode, D 2 (typically a HP 5082–4484); and a momentary test switch SW 6 are series connected from the output of A 5 to COMMON. When SW 6 is closed with the output of A 5 high, D 2 will light. Amplifier A 5 may be reset to the low output condition by opening switch SW 4 to remove power from the circuit. Resistor R 22 (typically 1 megohm) is connected from the noninverting input of A 5 to COMMON to assure that A 5 does not inadvertantly go to the high output condition when power is first applied to the circuit. The anode of diode CR 5 (typically a type IN 4148) is connected from the output of A 4 to resistor R 19 (typically 100 K ohm) which is in turn connected to the non-inverting input of A 5 coupling the signal from A 4 into the low flow detector circuit. The forward voltage drop of CR 5 helps prevent spurious signals from falsely tripping the low flow detector. In this configuration, the circuit normally requires 35 seconds after flow is interrupted until the circuit trips. This time can be decreased by increasing the ratio of R 20 to R 21.

The battery check circuit of FIG. 3 incorporates a network of NPN silicone transistors, Q 4 – Q 6, to provide a bias voltage that is stable with temperature changes. Resistor R 25 is connected from the + BUS to point A. Resistor R 26 is connected from point A to the junction of the base of Q 4, the collector of Q 4, and the base of Q 5. The emitters of Q 4 and Q 6 are connected to COMMON and the emitter of Q 5 is connected to COMMON through resistor R 28. Resistor R 27 is connected from point A to the junction of the collector of Q 5 and the base of Q 6. The collector of Q 6 is connected to point A. The resistors R 25 through R 28 are selected to give the best temperature stability of the voltage at point A. The voltage at point A typically is 1.5 volts. Resistor R 29 is connected from + BUS to the inverting input of A 6. Resistor R 30 is connected from the non-inverting input of A 6 to COMMON. The values of R 29 and R 30 are chosen to suit the desired battery test voltage. Resistor R 31 is connected from the output of A 6 to light emitting diode D 3. The other side of D 3 is connected to SW 6 similar to D 2. The other side of SW 6 is connected to COMMON.

In practical operation of the chemical dosimeter, a worker is given the dosimeter to wear for an 8 hour work shift. At the end of the shift, the circuit is tested to determine if the intake was blocked during the period by observing the light emitting diode (D 2 of FIG. 2) while pressing the momentary switch (SW 6 of FIG. 3. If the diode lights, blockage has taken place during the shift. The filter is then removed from the dosimeter and sent to a laboratory for analysis and the results are recorded in the worker's files. If there is excessive exposure, the worker can be withdrawn from the particular area and given another job.

It is practical to maintain a chemical dosimeter bank from which each worker draws his own dosimeter at the beginning of his work shift and is returned at the end of the shift.

It may be preferred to monitor only one worker of a given group and assume that the entire group has received the same exposure. If desired, individual dosimeters can be statically mounted in specific work areas and individual exposure can be approximated according to the time spent by the worker in a particular area.

The constant flow pump can also be used to fill a sample collection bag connected to the exhaust of the pump. This would provide a sample representative of the average gas present during the sampling period.

Under some circumstances, it may be practical to encapsulate the entire electrical circuit used in the dosimeter into a compact module using conventional compounds. This would provide a long service life under demanding environmental conditions and increase reliability in monitoring with a large number of dosimeters.

The invention claimed is:

1. An improved dosimeter for individual use that has an electric motor, a power source, an exhaust port and a filter means in which particles or vapors present in an air stream being pumped through the dosimeter are collected on the filter means; the improvement in use therewith comprises
    a variable drive pump tubularly connected to the filter means and coupled to the electric motor draws the air stream through the filter means;
    an air reservoir connected to the pump into which the air stream is being pumped retains excess air supplied by the pump and maintains a constant flow rate of the air stream;
    an orifice comprising an adjustable needle valve being positioned in a tube attached to the air reservoir and to the exhaust port, wherein the air stream is pumped through the orifice and thereby creates an air pressure drop;
    a differential pressure switch positioned in a tube connected to the exhaust port and in parallel to the orifice is activated by a change in the air pressure drop of the air stream and creates a low voltage electrical input signal;
    an integrator circuit electrically connected to a power source and to the pressure switch uses the low voltage input signal generated by the pressure switch and integrates this signal;
    an amplifier circuit electrically connected to the power source and connected in series to the integrator circuit and to the electric motor which amplifies the signal generated by the integrator circuit and feeds the amplified signal to the electric motor, thereby controlling the speed of the motor driving the pump in relationship to the signal generated by the pressure switch to maintain the air stream at a constant flow rate.

2. The improved dosimeter of claim 1 in which the variable drive pump is a diaphragm pump.

3. The improved dosimeter of claim 1 in which the pressure switch is activated by an air pressure drop of 3 inches of water and an air pressure drop change of 0.1 to 0.5 inch of water.

4. The improved dosimeter of claim 1 in which the integrator circuit is biased at about +0.6 volts and the signal from the integrator gradually increases to about +1.2 volts when the pressure switch is activated and gradually decreases to +0.6 volts when the switch is deactivated.

5. The improved dosimeter of claim 1 in which the amplifier circuit amplifies the signal from the integrator circuit to a maximum of about 96% of the total voltage of the power source and has an impedance of greater than 10 ohms.

6. The improved dosimeter of claim 1 in which the amplifier circuit amplifies the signal from the integrator circuit to a maximum of about 96% of the total voltage of the power source and has an impedance of less than 10 ohms.

7. The improved dosimeter of claim 1 which has electrically attached thereto a low air flow detector circuit comprising a bistable multivibrator circuit electrically connected to an indicator light.

8. The improved dosimeter of claim 1 which has electrically attached thereto a battery test circuit comprising a precision voltage detector adjusted to the voltage of each cell of the battery.

9. The improved dosimeter of claim 1 in which
    the variable drive pump is a diphragm pump;
    the orifice is an adjustable needle valve;
    the air pressure switch is activated by an air pressure drop of about 3 inches of water and by an air pressure drop change of about 0.1 to 0.5 inch of water;
    the integrator circuit is biased about +0.6 volts and the signal from the circuit gradually increases to about +1.2 volts when the pressure switch is activated and gradually decreases to +0.6 volts the pressure switch is deactivated;
    the amplifier circuit amplifies the signal from the integrator circuit to a maximum of about 96% of the total voltage of the power source and has impedance less than 10 ohms;
    the power source is a battery that has a maximum of 5.5 volts and has nickel cadmium cells; and has electrically connected thereto a low flow air detector circuit comprising a bistable multivibrator circuit electrically connected to an indicator light; and a battery test indicator circuit comprising a precision voltage detector adjusted to 5.2 volts.

10. A constant air flow sampling mechanism having an air inlet, an electric motor, a power source and an exhaust port which comprises a variable drive pump tubularly connected to the air inlet and coupled to an electric motor draws an air stream in through the inlet;

an air reservoir connected to the pump into which an air stream is being pumped retains excess air supplied by the pump and maintains constant flow rate of the air stream;

an orifice comprising an adjustable needle valve being positioned in a tube attached to the air reservoir and the exhaust port, wherein the air stream is pumped through the orifice and thereby creates an air pressure drop;

a differential pressure switch positioned in a tube connected to the exhaust port and in parallel to orifice is activated by a change in the air pressure drop of the air stream and creates a low voltage electrical input signal;

an integrator circuit electrically connected to a power source and to the pressure switch uses the low voltage input signal generated by the pressure switch and integrates this signal;

an amplifier circuit electrically connected to the power source and connected in series to the integrator circuit and to the electric motor which amplifies the signal generated by the integrator circuit and feeds an amplified signal to the electric motor, thereby controlling the speed of the motor driving the pump in relationship to the signal generated by the pressure switch to maintain the air stream at a constant flow rate.

* * * * *